United States Patent [19]

Mathur et al.

[11] Patent Number: 4,829,246
[45] Date of Patent: May 9, 1989

[54] APPARATUS HAVING INDUCTIVELY COUPLED COAXIAL COILS FOR MEASURING BUILDUP OF SLAY OR ASH IN A FURNACE

[75] Inventors: Mahendra P. Mathur, Pittsburgh; James M. Ekmann, Bethel Park, both of Pa.

[73] Assignee: The United States Department of Energy, Washington, D.C.

[21] Appl. No.: 16,900

[22] Filed: Feb. 20, 1987

[51] Int. Cl.$^4$ .................. G01N 27/72; G01R 33/12; F23B 1/00
[52] U.S. Cl. .................. 324/204; 110/349; 324/219; 324/226; 324/239
[58] Field of Search .............. 324/204, 219, 220, 226, 324/227, 239; 73/61.2, 661; 340/603; 110/185, 349

[56] References Cited

U.S. PATENT DOCUMENTS

| | | | |
|---|---|---|---|
| 2,104,644 | 1/1938 | Greenslade | 324/227 X |
| 3,152,303 | 10/1964 | Lary et al. | 324/204 |
| 3,164,993 | 1/1965 | Schmidt | 324/239 X |
| 3,838,372 | 9/1974 | Damijonaitis | 324/239 |
| 4,019,130 | 4/1977 | Sakamoto et al. | 324/219 |
| 4,027,233 | 5/1977 | Shmakov et al. | 324/204 X |
| 4,219,805 | 8/1980 | Magee et al. | 324/204 X |
| 4,511,371 | 4/1985 | Blaskowski | 48/197 R |
| 4,552,098 | 11/1985 | Wynnyckyj et al. | 122/379 |
| 4,556,019 | 12/1985 | Wynnyckyj et al. | 122/379 |

FOREIGN PATENT DOCUMENTS 1174326  9/1984  Canada ............ 110/185

OTHER PUBLICATIONS

Abstract Submitted For The March 1986 Meeting of The American Physical Society, Nov. 27, 1985.

Primary Examiner—Gerard R. Strecker
Attorney, Agent, or Firm—Hugh W. Glenn; Paul A. Gottlieb; William R. Moser

[57] ABSTRACT

The buildup of slag or ash on the interior surface of a furnace wall is monitored by disposing two coils to form a transformer which is secured adjacent to the inside surface of the furnace wall. The inductive coupling between the two coils of the transformer is affected by the presence of oxides of iron in the slag or ash which is adjacent to the transformer, and the application of a voltage to one winding produces a voltage at the other winding that is related to the thickness of the slag or ash buildup on the inside surface of the furnace wall. The output of the other winding is an electrical signal which can be used to control an alarm or the like or provide an indication of the thickness of the slag or ash buildup at a remote location.

1 Claim, 4 Drawing Sheets

4,829,246

APPARATUS HAVING INDUCTIVELY COUPLED COAXIAL COILS FOR MEASURING BUILDUP OF SLAY OR ASH IN A FURNACE

CONTRACTUAL ORIGIN OF THE INVENTION

The U.S. Government has rights in this invention as a result of the employment of the inventors by the U.S. Department of Energy.

BACKGROUND OF THE INVENTION

This invention relates to apparatus for monitoring the thickness of slag or ash in a furnace.

Coal typically contains silica, alumina and one or more of the oxides of iron, in addition to relatively small quantities of other metal oxides. These components are incombustible, and form slag or ash when the coal is burned. Slag is a fluid or solid agglomeration of the incombustible portion of burned coal, while ash is the same material in the form of fine particles that are not fused or agglomerated. A problem that results from burning coal in furnaces is the effect of the incombustible components of the coal on the operation of the furnace. This is particularly a problem when the coal is pulverized to improve combustion.

One requirement for efficient operation of a furnace is good heat exchange between the hot combustion products of coal and the water that is to be heated. When the incombustible portions of the coal, whether in the form of molten ash or solid particles, come into contact with the heat-exchange surfaces such as water walls and boiler tubes, the particles tend to adhere to the heat-exchange surfaces and interfere with heat transfer, creating slag or ash buildup. As a result of such slag or ash buildup, the capacity of the furnace is typically reduced. To maintain the capacity of the furnace, the heat-exchange surfaces are cleaned periodically by blowing steam or hot air through the furnace or by other suitable processes.

Slag or ash buildup is a particular problem in some oil or gas furnaces that are converted to burn coal, since oil and gas furnaces do not tend to collect as much slag or ash and their interiors are designed accordingly. The incombustible products of the combustion of coal tend to be abrasive, and in the cleaning process, the incombustibles erode internal furnace components of such coal furnaces. It is therefore preferable to clean the furnace of slag or ash accumulations only when it is necessary. However, the expense and loss of time incurred in measuring furnace slag or ash buildup by the visual internal inspection has created a need for apparatus which measures slag or ash buildup without internal visual inspection.

U.S. Pat. No. 4,552,098, entitled "Convection Section Ash Monitoring," discloses apparatus for monitoring the thickness of ash in furnaces. That patent teaches the use of radiation pyrometers to measure temperature drop as combustion products pass a bank of heat exchanger tubes. A fouling factor is calculated from the data generated by the pyrometers, and the fouling factor is a known or calculable function of the accumulation of incombustible material on the heat exchanger. Thus, the apparatus determines slag or ash buildup indirectly, in a manner which requires additional calculation. In addition, the radiation pyrometers of the '098 patent provide only an average indication of fouling.

In U.S. Pat. No. 4,511,371, the buildup of slag or ash in the combustor is monitored visually. This apparatus obviously requires human presence, which is not always desirable or possible. Thus, there is a need for apparatus for monitoring slag or ash buildup in furnaces without internal visual inspection which does not require processing of data or human inspection.

SUMMARY OF INVENTION

Accordingly, it is an object of the present invention to provide new and improved apparatus for measuring the thickness of slag or ash buildup in a furnace.

It is a further object of the present invention to provide new and improved apparatus for measuring slag or ash buildup in a furnace without internal visual inspection.

It is also an object of the present invention to provide new and improved apparatus for monitoring slag or ash buildup in a furnace without significant data processing.

It is yet another object of the present invention to provide new improved apparatus for monitoring slag or ash buildup in a furnace without human presence.

Other objects will become apparent in the course of a detailed description of the invention.

In keeping with one aspect of this invention, the buildup of slag or ash in the interior of a furnace is monitored by measuring the output voltage of a transformer which is in a probe that is secured adjacent to the inside surface of the furnace wall. The inductive coupling between the two coils of the transformer is affected by the presence of oxides of iron in the slag or ash which is adjacent to the transformer, and the output voltage of the transformer is related to the thickness of the slag or ash buildup on the probe and hence on the inside surface of the furnace. The output of the transformer is an electrical signal which can be used to control an alarm or provide an indication of the thickness of the slag or ash buildup at a remote location.

BRIEF DESCRIPTION OF THE DRAWINGS

The above mentioned and other features of this invention and the manner of obtaining them will become more apparent, and the invention itself will be best understood, by reference to the following description of the invention taken in conjunction with the accompanying drawings, in which.

DETAILED DESCRIPTION

Figure 1:
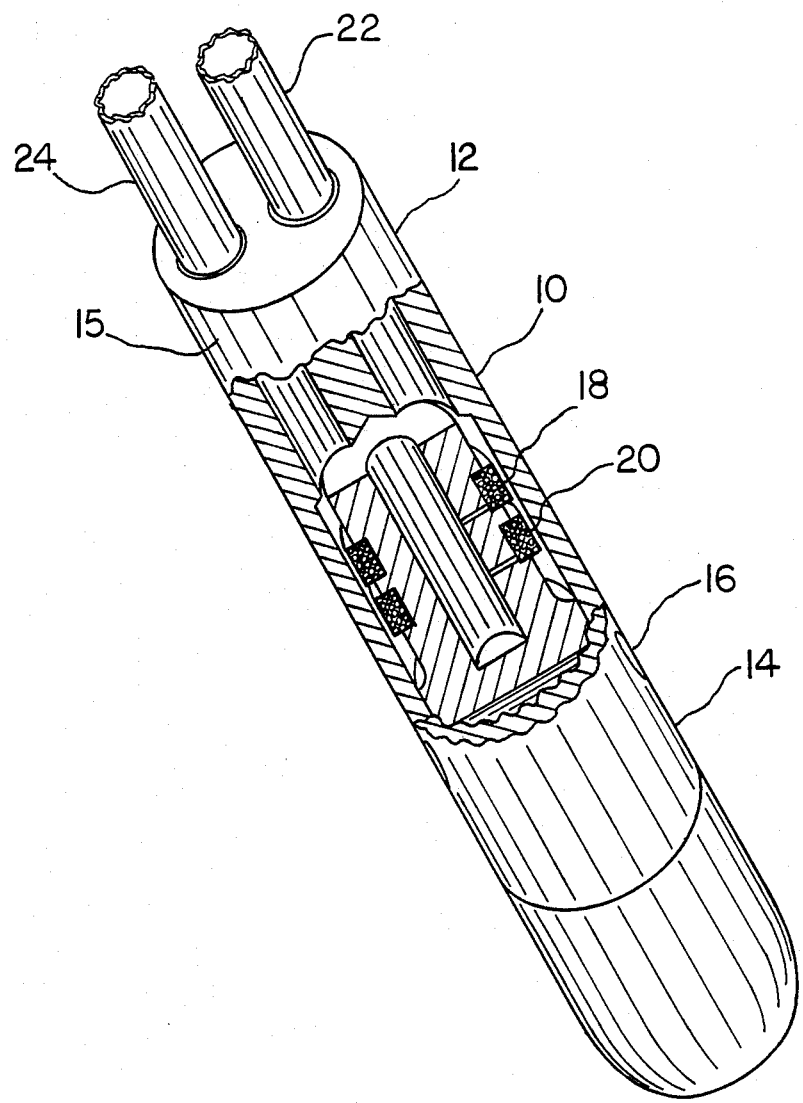
FIG. 1 is a cutaway perspective view of the apparatus made in/accordance with the present invention.

FIG. 1 is a cutaway perspective view of the apparatus 10 for measuring the thickness of slag or ash buildup in a furnace. The apparatus 10 includes a base 12 and a tip 14 that are assembled together to form a housing 15. The base 12 and the tip 14 are held in place by a bolt 16.

The tip 14 includes two coils 18 and 20 which are placed or wound coaxially on the tip 14.

Two tubes 22 and 24 are provided in the base 12. The tubes 22 and 24 provide access from outside a furnace wall to the interior of the apparatus 10 so that electrical connections can be made with the coils 18 and 20. The tubes 22 and 24 also permit the circulation of a gas such as nitrogen in the apparatus 10 to cool the inside of the apparatus 10.

The base 12 and tip 14 may be made of a ceramic material such as alumina or silica or the like, or of a non-ferromagnetic metal such as nonmagnetic stainless steel, aluminum, or the like. The tubes 22 and 24 are preferably made of copper, stainless steel, or aluminum.

Figures 2, 3:
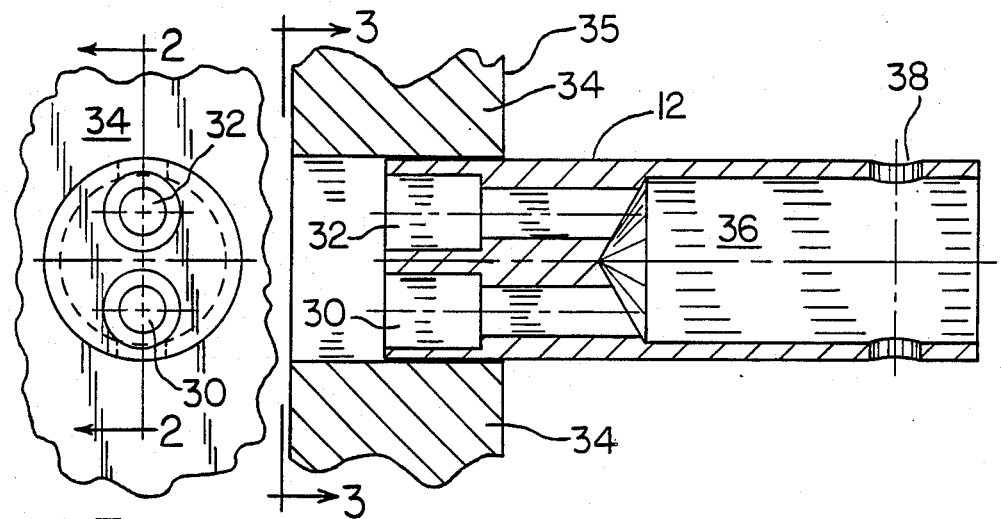
FIG. 2 is a side view of a portion of the apparatus of FIG. 1, shown installed in a furnace wall.
FIG. 3 is an end view of the portion of the apparatus shown in FIG. 2.

FIG. 2 shows a portion of the base 12 of FIG. 1 secured in a furnace wall 34. FIG. 3 is an end view of the structure shown in FIG. 2. In FIGS. 2 and 3, orifices 30 and 32 are provided in the base 12 to receive the tubes 22 and 24 of FIG. 1. The base 12 is preferably positioned in the furnace wall 34 so that the orifices 30 and 32 open toward the outside of the wall 34 and the bulk of base 12 is secured adjacent to an inside surface 35 of the furnace wall 34. The orifices 30 and 32 also project into a chamber 36 in the apparatus 10 so that wires may pass from the chamber through the orifices 30 and 32 and out of the apparatus 10 on the outside of the furnace wall 34. An opening 38 extends through the base 12 and the chamber 36 to receive a bolt (not shown).

Figures 4, 5:
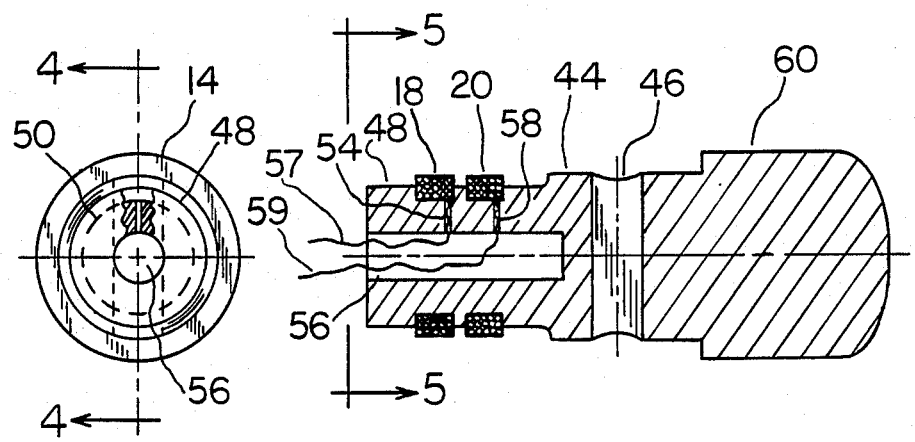
FIG. 4 is a side view of another portion of the probe of FIG. 1.
FIG. 5 is an end view of the portion of the apparatus shown in FIG. 4.

FIG. 4 is a side view and FIG. 5 is an end view of the tip 14 of FIG. 1. The tip 14 fits into the base 12 in the manner shown in FIG. 6. In FIGS. 4 and 5, the tip 14 includes a shoulder 44 which is sized to make a snug fit with the chamber 36 of FIG. 2 when the tip 14 is inserted into the base 12. An opening 46 is located and sized to align with the opening 38 of FIG. 2 when the tip 14 is so inserted. A core 48 is provided adjacent to the shoulder 44. The core 48 is reduced in diameter from the diameter of the shoulder 44 so as to extend into the chamber 36 of FIG. 2 and provide support for and allow clearance for the windings 18 and 20. An opening 54 carries wires 57 from the winding 18 to an opening 56, and an opening 58 carries wires 59 from the winding 20 into the opening 56. The wires 57 and 59 from the windings 18 and 20, respectively, are taken through the opening 56, through the orifices 30 and 32 of FIG. 2, and are thus made available for electrical connections outside the furnace wall 34 of FIG. 2. A projection 60 in the tip 14 (FIG. 4) completes the closure of the chamber 36 of FIG. 2, physically protecting the windings 18 and 20 from the hostile environment inside the furnace.

Figure 6:
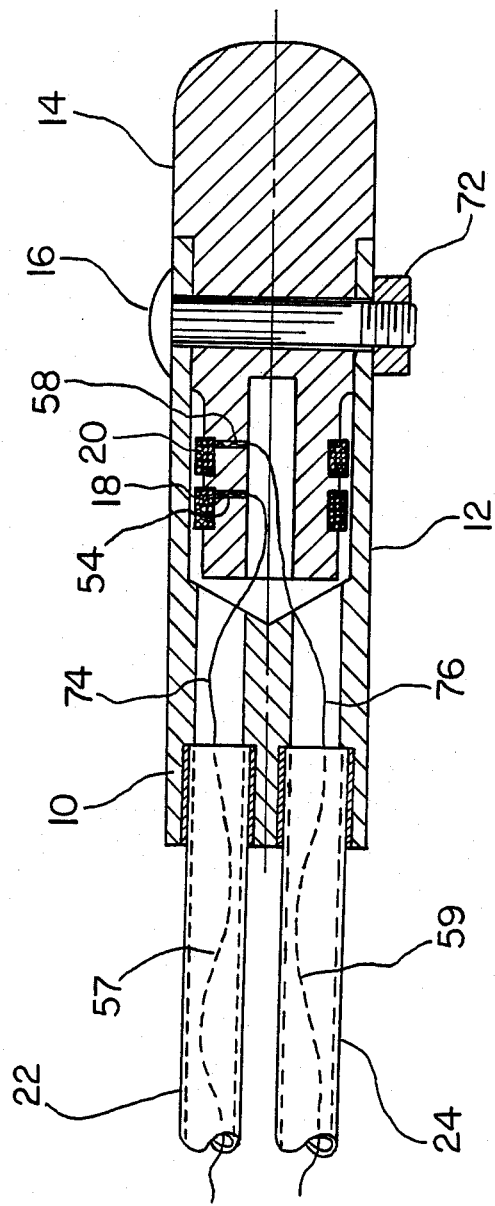
FIG. 6 is a cross-sectional side view of the apparatus of FIG. 1.

FIG. 6 is a sectional side view of the apparatus 10 as assembled. In FIG. 6, the bolt 16 and a nut 72 hold the tip 14 in place in the base 12. The wires 57 are electrically connected to the winding 18 and extend through the tube 22, and the wires 59 are electrically connected to the winding 20 and extend through the tube 24.

The tubes 22 and 24 may be secured to the base 12 by cementing, brazing, gluing, or the like. The windings 18 and 20 may have approximately 575 turns each of number 30 copper wire, or any other suitable configuration.

In use, one of the windings 18 or 20 is excited with a sinusoidal voltage at a constant amplitude and a predetermined frequency. The magnetic field generated by current flow in the excited winding induces an output voltage in the adjacent winding. The magnitude of the output voltage is related to the inductive coupling between the windings 18 and 20.

Both ash and slag on the walls of a coal-burning furnace contain ferromagnetic materials. The presence of these materials near the apparatus 10 affects the coupling between the windings 18 and 20, and, hence, affects the output voltage of the apparatus 10. The presence of ferromagnetic material is indicated by Table 1, which is a tabulation of the results of an analysis of ash constituents of a typical eastern bituminous coal.

TABLE 1

Composition of Fly Ash and Deposits

| Constituents % Wt | Fly Ash | Superheater Deposits (Outerlayer) |
|---|---|---|
| $SiO_2$ | 37.4 | 36.2 |
| $Al_2O_3$ | 15.3 | 12.9 |
| $Fe_2O_3$ | 20.8 | 19.9 |
| $TiO_2$ | 1.0 | 1.1 |
| CaO | 5.2 | 9.1 |
| MgO | 0.9 | 1.0 |
| $Na_2O$ | 3.8 | 4.3 |
| $K_2O$ | 2.7 | 2.4 |
| $SO_3$ | 9.6 | 13.1 |
| Not Determined | 3.3 | 0.0 |
| Total | 100 | 100 |

It is evident from an inspection of Table 1 that both the fly ash and the deposits removed from the super heater are approximately 20% ferric oxide, a ferromagnetic material. The development of an indication of the presence of ferric oxide and its approximate extent thus provides a useful measure of the buildup of deposits on the probe within the furnace.

Figure 7:
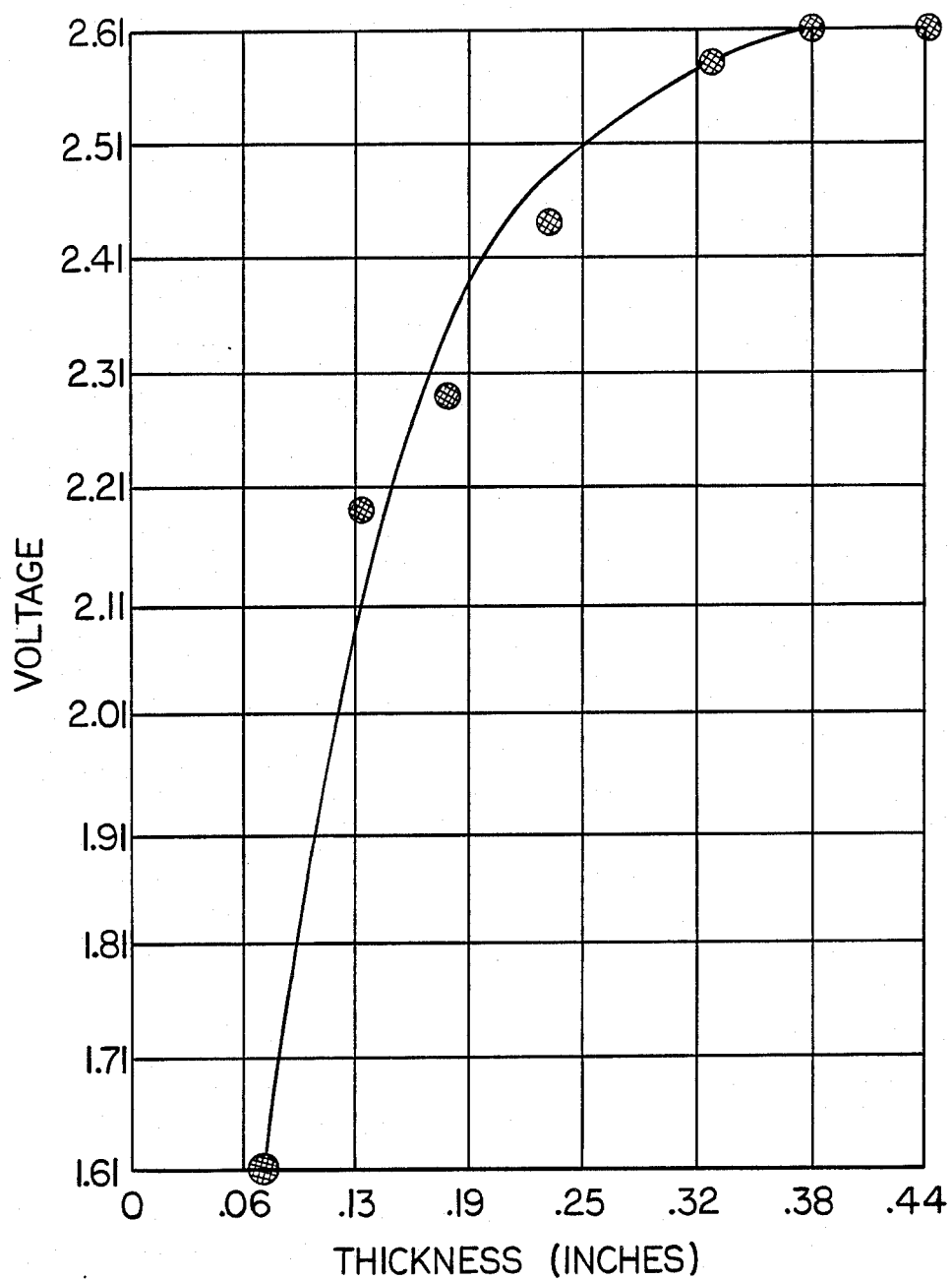
FIG. 7 is a plot of the electrical output of the apparatus of FIG. 1 showing the relationship between output voltage and slag or ash buildup as measured at 30 kilohertz.

FIG. 7 is a graph of the output voltage as a function of slag or ash thickness measured at about 30 kilohertz by use of the apparatus of the present invention. It may be seen from FIG. 7 that, in the slag or ash thickness range of zero to 0.4 inches, the output voltage varies noticeably with a change in the thickness of the slag or ash.

The inventors contemplate the use of frequencies in the range of about 10 to 100 kilohertz in making measurements with the apparatus of the present invention.

The many advantages of this invention are now apparent. Slag or ash thickness on the inside surface of a furnace wall may be measured without internal visual inspection. Observation of the output voltage provides information to an operator about the thickness of slag or ash buildup in the furnace and enables the operator to operate soot blowers or other furnace cleaners at optimum intervals to provide an appropriate limitation of the amount of buildup allowed, without unnecessary cleaning. The electrical output of the apparatus may be used to control an alarm, a soot blower or the like. The electrical output also allows the slag or ash buildup to be monitored from a remote location.

While in the foregoing specification this invention has been described in connection with specific apparatus and applications, it is to be understood that this description is made by way of example, and not as a limitation on the scope of the invention.

The embodiments of the invention in which an exclusive property or privilege is claimed are defined as follows:

1. Apparatus adapted for securement within an aperture in a wall of a furnace to extend through said wall into the furnace to measure slag or ash buildup on an inside surface of the furnace wall by measuring such buildup on the apparatus, the slag or ash having a known quantity of iron oxides, the apparatus comprising:

a. a tip having a shoulder portion and a core portion of a diameter less than the diameter of said shoulder portion;

b. a base having an outside diameter substantially equal to the diameter of said shoulder portion of said tip and a chamber having a diameter greater than the diameter of said core portion of said tip, said core portion of said tip being inserted in said chamber and secured to said base so that said shoulder portion of said tip contacts said base to seal said chamber from the inside of the furnace;

c. a first coil wound coaxially on said core portion of said tip and thereby secured in said sealed chamber adjacent the wall;

d. a second coil wound coaxially on said core portion of said tip and thereby secured in said sealed chamber adjacent the wall and said first coil so as to couple inductively with said first coil; and e. orifice means in said base for permitting access to said sealed chamber through the aperture in the furnace wall and for passing coolant to and from said sealed chamber for cooling said apparatus;

whereby buildup of slag or fly ash on said base and said tip affects inductive coupling between said first and second coils, which inductive coupling is a measure of buildup of fly ash or slag on said base and tip and hence is a measure of buildup on the inside surface of the furnace wall.

* * * * *